US00PP29362P3

(12) United States Plant Patent
Olesen

(10) Patent No.: US PP29,362 P3
(45) Date of Patent: Jun. 12, 2018

(54) CLIMBING ROSE PLANT NAMED 'POULCY035'

(50) Latin Name: ***Rosa* hybrid**
Varietal Denomination: Poulcy035

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 67 days.

(21) Appl. No.: 15/330,295

(22) Filed: Sep. 6, 2016

(65) Prior Publication Data

US 2018/0070490 P1 Mar. 8, 2018

(51) Int. Cl.
*A01H 5/02* (2018.01)

(52) U.S. Cl.
USPC ..... Plt./112
CPC ..... *A01H 5/0222* (2013.01)

(58) Field of Classification Search
USPC ..... Plt./112
See application file for complete search history.

*Primary Examiner* — Keith O Robinson

(57) ABSTRACT

A new garden rose plant of the Climbing class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy035'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulcy035', originated as a single seedling from the stated cross.

The new variety may be distinguished from its male pollen parent and female seed parent by the following characteristics. The male pollen parent plant has dark red flowers, and grows to 45 cm in height in one season, while the claimed plant has orange red flowers and grows to a height of 120 cm in one season. The female seed parent plant has flowers which are about 25 mm in diameter and grows to a height of 65 cm in one season, while the new variety has flowers which are 45 mm in diameter and grows to a height of 120 cm in one season.

The objective of the hybridization of this rose variety was to create a new and distinct variety for garden use with unique qualities, such as:

1. Uniform and abundant orange red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.
5. Has a climbing habit, yet more compact than traditional climbing roses.

This combination of qualities is not present in previously available commercial cultivars of this type, known to the inventor, and distinguish 'Poulcy035' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulcy035' was selected in the spring of 2008 by the inventor as a single plant from the progeny of the aforementioned hybridization.

Asexual reproduction of 'Poulcy035' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulcy035' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy035'.

Specifically illustrated in FIG. 1 are open flowers, petals detached, sepals, and reproductive flower parts.

DETAILED DESCRIPTION OF THE VARIETY

Figure 1:
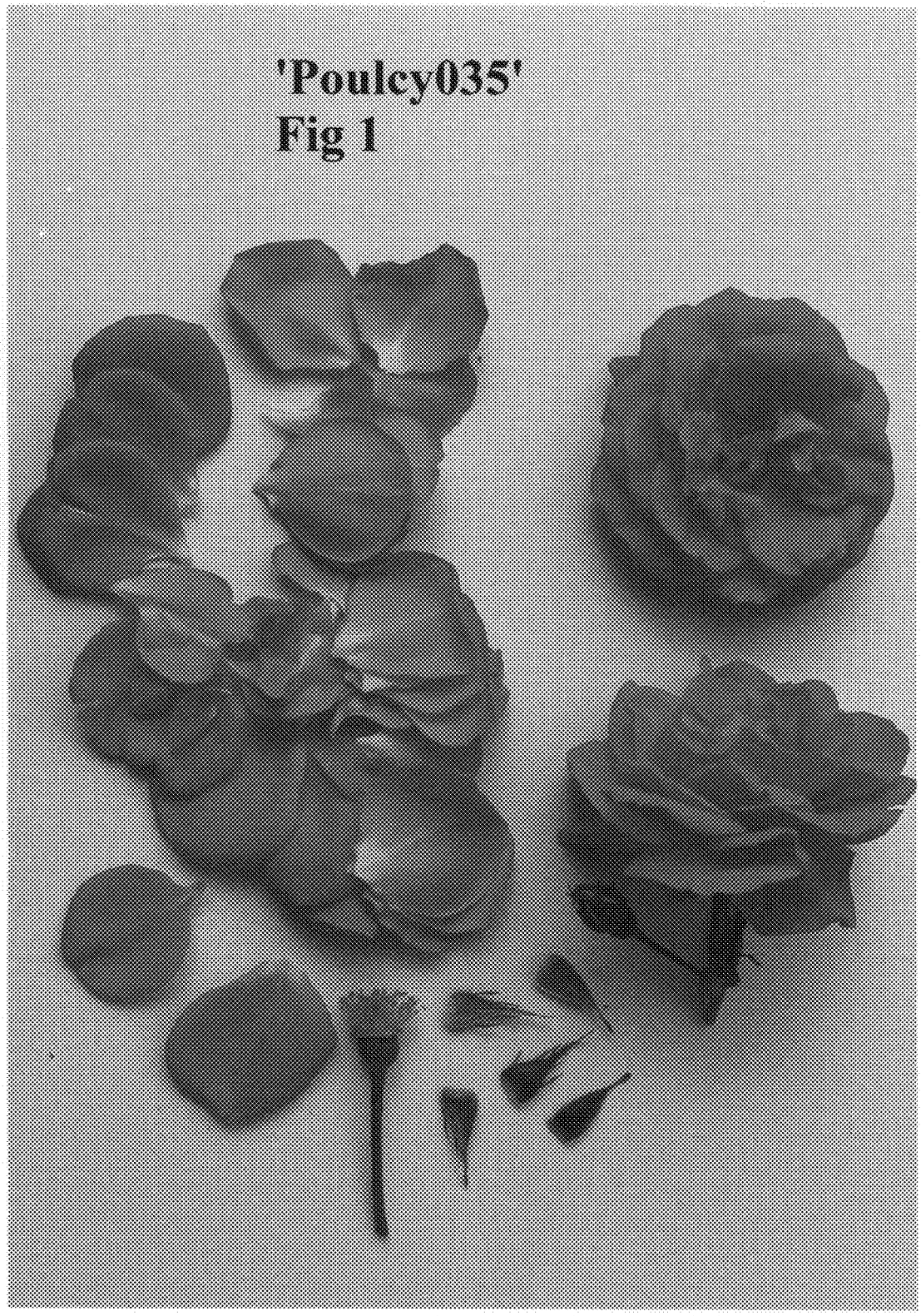
Figure 2:
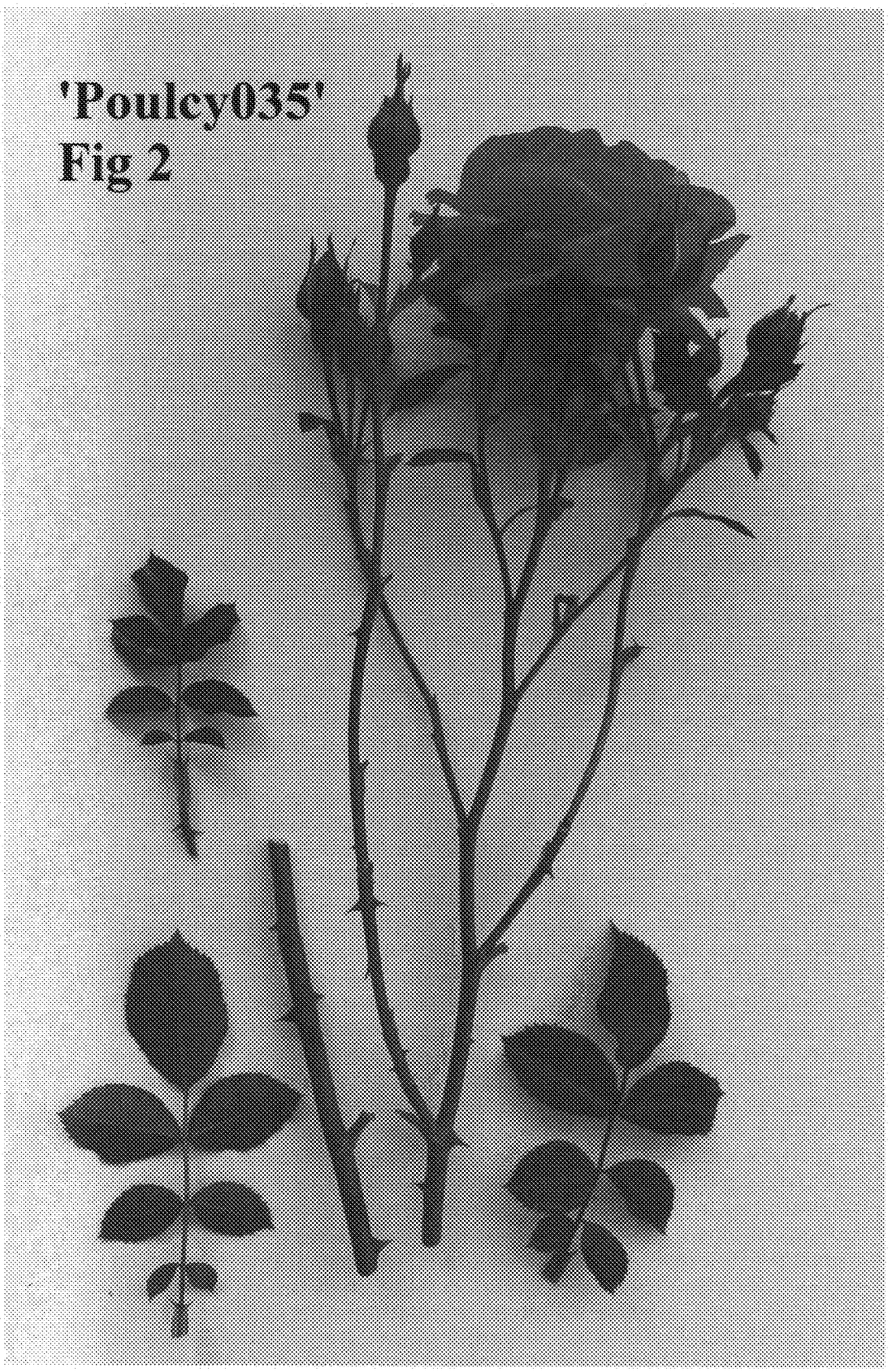
In FIG. 2 of the drawings are leaves, bare stems, and a flowering branch showing peduncles. Plants shown are 2 years of age.

The following is a description of 'Poulcy035', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulyc009', U.S. Plant Pat. No. 15,411 are compared to 'Poulcy035' in Chart 1.

CHART 1

| | 'Poulcy035' | 'Poulyc009' |
|---|---|---|
| Petal Count | 35 to 40 | 25 |
| Flower Diameter | 85 mm | 70 mm |
| General Tonality of Flower Color | Red Group 40A | Red-Purple 58B to 58C |

FLOWER AND FLOWER BUD

Blooming habit: Continuous.

Flower bud:

*Size*.—Upon opening, 27 mm in length from base of receptacle to end of bud. Bud diameter is 15 mm.

*Bud form*.—Ovoid.

*Bud color*.—As sepals divide petals are Red Group 42A.

*Sepal inner surface*.—Color: Yellow-Green Group 145C with strong intonations of Greyed-Purple Group 183B. Surface: Lightly pubescent.

*Sepal outer surface*.—Color: Yellow-Green Group 144A with intonations of Greyed-Red Group 180A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—27 mm long, 10 mm wide.

*Receptacle*.—Texture: Smooth. Size: 7 mm in height, 8 mm wide. Color: Yellow-Green Group 144A with intonations of Greyed-Red Group 181A. Shape: Slightly globose.

*Pedicel*.—Surface: Small prickles. Length: About 30 mm. Diameter: 3 mm on average. Color: Yellow-Green Group 144A with intonations of Greyed-Red Group 181A. Strength: Strong.

*Peduncle*.—Length: 20 to 40 cm. Diameter: About 4 mm. Color: Yellow-Green Group 144A. Texture: Smooth.

Flower bud development: Flower buds are borne in clusters up to 15 flower buds per stem. Development as a corymb.

Flower bloom:

*Fragrance*.—None.

*Duration*.—The blooms have a duration on the plant of approximately 7 to 10 days. Petals fall cleanly away from plant after flowers have fully matured.

*Size*.—Flower diameter is 85 mm when open. Flower depth is 40 mm.

*Flower shape*.—Open cup.

Petalage: Under normal conditions, flowers have 35 to 40 petals total, 5 of which are petaloids.

General tonality of flower: Open flowers are Red Group 40 A.

Petal color upon and after opening:

*Outer petals*.—Upper surface: Red Group 40A. Lower surface: Red Group 43C.

*Inner petals*.—Upper surface: Red Group 40A. Lower surface: Red Group 43C.

*Basal petal spots*.—Upper surface: Yellow Group 4D. Lower surface: Yellow Group 4D and White Group 155A.

Petals:

*Petal reflex*.—Somewhat reflexed.

*Margin*.—Entire and uniform. Moderate undulations.

*Shape*.—Broad elliptic. Apex shape: Rounded. Base shape: Acute.

*Size*.—50 mm (l) 45 mm (w).

*Texture*.—Smooth.

*Thickness*.—Average.

Petaloids:

*Size*.—25 mm (l) by 10 mm (w).

*Quantity*.—About 5.

*Shape*.—Asymmetric, with a rounded apex and acute base.

*Color*.—Upper surface Red Group 40A and a petaloid spot of Yellow Group 4D. Lower surface Red Group 43C and a petaloid spot of Yellow Group 4D with shades of White Group 155A.

Reproductive flower parts:

*Pollen*.—None observed.

*Anthers*.—Size: 2 mm in length. Color: Greyed-Orange Group 167B. Quantity: 45 on average.

*Filaments*.—Color: Yellow-Orange Group 15C. Length: 5 mm.

*Pistils*.—Length: 8 mm. Quantity: 25 on average.

*Stigmas*.—Color: Yellow-White Group 158C.

*Styles*.—Color: White Group 155A with intonations of Red Group 37C.

*Location of stigmas*.—Superior in location relative to the length of the filaments and the height of the anthers.

*Hips*.—None Observed.

PLANT

Plant growth: Upright, climbing habit. Plants are 120 cm in height, and 90 cm wide.

Stems:

*Color*.—Juvenile growth: Yellow-Green Group 144B. Mature growth: Yellow-Green Group 144A.

*Length*.—On average, canes are 50 cm from the base of the plant to the flowering portion.

*Diameter*.—6 mm.

*Internodes*.—On mature canes about 45 mm between nodes.

*Surface texture*.—Young wood: Smooth. Older wood: Smooth.

Long prickles:

*Incidence*.—7 prickles per 10 cm of stem.

*Size*.—Average length of prickles on mature stems is 8 mm.

*Shape*.—Upper portion is linear. Lower portion is concave.

*Color*.—Juvenile prickles: Greyed-Red Group 180A. Mature prickles: Greyed-Orange Group 173A.

Plant foliage:

*Compound leaf*.—145 mm (l)×70 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 30 mm long, 8 mm wide. Quantity: 2 per compound leaf. Shape: Linear, slightly broad based with outward extending apices. Margins: Finely serrated. Color: Yellow-Green Group.

*Petiole*.—Length: 33 mm. Diameter: 2 mm.

*Upper surface*.—Color: Greyed-Purple Group 185A.

*Lower surface*.—Color: Yellow-Green Group 144A.

*Rachis*.—Length: 55 mm. Upper surface: Color: Greyed-Purple Group 185A.

*Lower surface*.—Color: Yellow-Green Group 144A.

*Leaflet*.—Quantity: Normally 5 leaflets. Margins: Serrated. Size: On average terminal leaflets are 45 mm long, 34 mm wide. Shape: Generally elliptical. Base: Obtuse. Apex: Cuspidate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Climbing rose class named 'Poulcy035', substantially as illustrated and described herein, due to its abundant orange red flowers, disease resistance, and extended period of bloom.

* * * * *

'Poulcy035'

'Poulcy035'